US012758755B2

(12) United States Patent
Lin et al.

(10) Patent No.: US 12,758,755 B2
(45) Date of Patent: Oct. 13, 2026

(54) DISSOLVABLE MICRONEEDLE PATCH AND METHOD TO PRODUCE DISSOLVABLE MICRONEEDLE PATCH

(71) Applicant: DARWIN PRECISIONS CORPORATION, Hsinchu County (TW)

(72) Inventors: Jen Shun Lin, Hsinchu County (TW); Jyun-Yi Yu, Hsinchu County (TW); Yunpei Yang, Hsinchu County (TW)

(73) Assignee: DARWIN PRECISIONS CORPORATION, Hsinchu County (TW)

( * ) Notice: Subject to any disclaimer, the term of this patent is extended or adjusted under 35 U.S.C. 154(b) by 544 days.

(21) Appl. No.: 18/232,842

(22) Filed: Aug. 11, 2023

(65) Prior Publication Data

US 2024/0350783 A1 Oct. 24, 2024

(30) Foreign Application Priority Data

Apr. 20, 2023 (TW) ................................ 112114730

(51) Int. Cl.

| | |
|---|---|
| ***A61M 37/00*** | (2006.01) |
| ***A61K 9/00*** | (2006.01) |
| *A61K 47/36* | (2006.01) |

(52) U.S. Cl.

CPC ....... *A61M 37/0015* (2013.01); *A61K 9/0021* (2013.01); *A61K 47/36* (2013.01); *A61M 2037/0023* (2013.01); *A61M 2037/0046* (2013.01); *A61M 2037/0053* (2013.01); *A61M 2037/0061* (2013.01)

(58) Field of Classification Search

CPC ...... A61M 37/0015; A61M 2037/0023; A61M 2037/0046; A61M 2037/0053; A61M 2037/0061; A61K 47/36; A61K 9/0021

See application file for complete search history.

(56) References Cited

FOREIGN PATENT DOCUMENTS

| | | | | | |
|---|---|---|---|---|---|
| CN | 107343984 | B | * | 2/2021 | ........ A61M 37/0015 |
| CN | 113144413 | A | | 7/2021 | |
| CN | 115252535 | A | | 11/2022 | |
| CN | 115463334 | A | | 12/2022 | |
| JP | 2024082115 | A | * | 6/2024 | |
| TW | 201600113 | A | | 1/2016 | |
| TW | 201902529 | A | | 1/2019 | |
| TW | M644219 | U | | 7/2023 | |

OTHER PUBLICATIONS

Translation/English of CN 10734984B (Year: 2021).*
Translation/english of JP 2024082115A (Year: 2026).*

* cited by examiner

*Primary Examiner* — Charles G Freay

(57) ABSTRACT

A dissolvable microneedle patch includes a microneedle portion and a patch portion. The microneedle portion has a base and a plurality of microneedles. The base has a first surface and a second surface opposite thereto. The microneedles are connected to the first surface. The patch portion is connected to the second surface. The microneedle portion is made from a mixture, and the mixture includes an excipient. The excipient includes sodium alginate and dextrin, and a weight ratio of the dextrin to the sodium alginate is 0.2 to 1. In addition, the present invention also provides a method to produce the dissolvable microneedle patch.

8 Claims, 5 Drawing Sheets

1

DISSOLVABLE MICRONEEDLE PATCH AND METHOD TO PRODUCE DISSOLVABLE MICRONEEDLE PATCH

FIELD OF THE INVENTION

The present invention relates to a patch, and more particularly to a dissolvable microneedle patch with dissolvable microneedles on the surface and a method to produce the dissolvable microneedle patch.

BACKGROUND OF THE INVENTION

A microneedle patch (MNP) is a transdermal drug delivery system (TDDS) that has the advantages of both a transdermal patch and subcutaneous injection. Because the microneedles are not that long to irritate the skin nerves, they are less painful. Because the microneedles can pierce the stratum corneum of the skin surface, it is convenient to carry large molecules of drugs through the stratum corneum and into the body. At present, the microneedles have been applied to the field of medical cosmetology.

The microneedle patch includes solid microneedles, coated microneedles, hollow microneedles, and dissolving microneedles depending on the type of microneedles on its surface. The dissolving microneedles are safer and have more development potential than other types of microneedles because they do not have the risk of remaining in the skin after the needles fracture.

SUMMARY OF THE INVENTION

The present invention provides a dissolvable microneedle patch, which has the advantages of a flat surface and low breaking tendency and does not have the problem of the curled film surface, skew or fractured microneedle structure, etc.

The present invention provides a method to produce the dissolvable microneedle patch. The produced microneedle patch has the advantages of flat surface and low breaking tendency and does not have the problem of curled film surface, skew or fractured microneedle structure, etc.

In order to achieve the above advantages, an embodiment of the present invention provides a dissolvable microneedle patch, including: a microneedle portion and a patch portion. The microneedle portion has a base and a plurality of microneedles. The base has a first surface and a second surface opposite thereto. The microneedles are connected to the first surface. The patch portion is connected to the second surface. The microneedle portion is made from a mixture, and the mixture includes an excipient. The excipient includes sodium alginate and dextrin, and a weight ratio of the dextrin to the sodium alginate is 0.2 to 1.

In an embodiment of the present invention, the microneedles have a height of 100 to 1500 μm.

In an embodiment of the present invention, the microneedles each have a shape of a pyramid or a cone.

In an embodiment of the present invention, the mixture further includes a functional ingredient selected from hyaluronic acid, salicylic acid, vitamin C, nicotinic acid, vitamin B5, sulfur, *Centella asiatica*, vitamin E powder, ceramide, glycerol, GLP-1, insulin, acetaminophen and combinations thereof.

The present invention further provides a method to produce the dissolvable microneedle patch, including the following steps: providing a mold formed with a plurality of grooves; injecting an aqueous solution into the mold, and drying the aqueous solution to form a microneedle substrate, the microneedle substrate including a plurality of microneedle portions, each of the microneedle portions including a base and a plurality of microneedles, and the microneedles each having a shape corresponding to that of the grooves each; gluing a plurality of patch materials to the microneedle portion; and cutting the microneedle substrate to form a plurality of the dissolvable microneedle patches. A mixture of an excipient and a functional ingredient is dissolved in the aqueous solution. The excipient includes sodium alginate and dextrin, and a weight ratio of the dextrin to the sodium alginate is 0.2 to 1.

In an embodiment of the present invention, the aqueous solution includes 1.5% by weight of the sodium alginate.

In an embodiment of the present invention, the aqueous solution of sodium alginate has a viscosity of 15 to 5000 cps.

In an embodiment of the present invention, the aqueous solution is dried at 30 to 60° C. for 1 to 6 hours.

Based on the above, according to the dissolvable microneedle patch of the present invention, the weight ratio of the sodium alginate to the dextrin in the excipient is adjusted, so the base of the produced dissolvable microneedle portion has a flat surface and low breaking tendency and is suitable for a nice fit with the patch portion, and the produced dissolvable microneedle patch does not have the problem of the curled film surface, skew or fractured microneedle structure, etc. According to the method to produce the dissolvable microneedle patch of the present invention, the weight ratio of the sodium alginate to the dextrin in the excipient is adjusted, so the produced microneedle patch has the advantages and features of the above-mentioned dissolvable microneedle patch.

Other objectives, features, and advantages of the invention will be further understood from the further technological features disclosed by the embodiments of the invention wherein there are shown and described preferred embodiments of this invention, simply by way of illustration of modes best suited to carry out the invention.

DETAILED DESCRIPTION OF PREFERRED EMBODIMENTS

Directional or positional relationships indicated by terms used in the description of embodiments according to the present invention, such as “upper” and “lower”, are described according to the directional or positional relationships shown in the accompanying drawings. The above terms are merely for the convenience of describing the present invention and are not intended to limit the present invention, i.e., they do not indicate or imply that the mentioned elements must have a specific orientation or be constructed in a specific orientation. In addition, the terms “first”, “second” and the like mentioned in the specification or the claims are used only to designate the names of the elements or to distinguish different embodiments or ranges and are not intended to limit the upper or lower limit of the number of elements.

Figure 1:
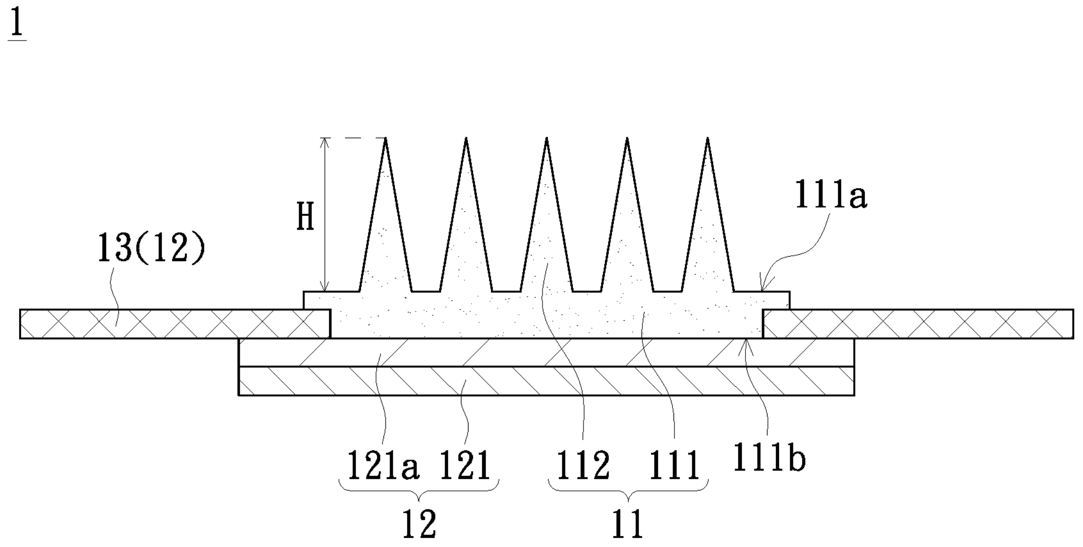
FIG. 1 is a schematic side view of a dissolvable microneedle patch according to an embodiment of the present invention.

FIG. 1 is a schematic side view of a dissolvable microneedle patch according to an embodiment of the present invention. Table 1 shows comparison of test results of different ratios of ingredients in the microneedle portion. As shown in FIG. 1, a dissolvable microneedle patch 1 in this embodiment of the present invention includes a microneedle portion 11 and a patch portion 12. The microneedle portion 11 has a base 111 and a plurality of microneedles 112. The base 111 has a first surface 111*a* and a second surface 111*b* opposite thereto. The microneedles 112 are connected to the first surface 111*a*. The patch portion 12 is connected to the second surface 111*b*. The microneedle portion 11 is made from a mixture, and the mixture includes an excipient. The excipient includes sodium alginate and dextrin, and a weight ratio of the dextrin to the sodium alginate is 0.2 to 1.

In different embodiments of the present invention, in addition to the excipient, the mixture of the produced microneedle portion 11 also includes a functional ingredient. The functional ingredient is, for example, an ingredient that will not affect the film forming result of the microneedle portion 11 during the production process. Specifically, the functional ingredient is, for example, but not limited to, hyaluronic acid, salicylic acid, vitamin C, nicotinic acid, vitamin B5, sulfur, *Centella asiatica*, vitamin E powder, ceramide, glycerol, GLP-1, insulin, acetaminophen and other ingredients used in medical treatment or medical cosmetology and combinations thereof, which may be selected according to the actual product requirements.

In different embodiments of the present invention, the microneedles 112 made from the mixture of the sodium alginate and the dextrin in the above ratio have a height H of 100 to 1500 μm, and have good mechanical properties and low fracture tendency during use. The microneedles each 112 have a shape of, for example, a pyramid or a cone, which may vary according to requirements (detailed in the method to produce the dissolvable microneedle patch).

As shown in FIG. 1, in this embodiment, the patch portion 12 includes, for example, a backing sheet 121 and a release film 13. One surface of the backing sheet 121 is provided with an adhesive film 121*a*. A part of the surface of the adhesive film 121*a* is bonded to a bottom of the microneedle portion 11, and the other part of the surface is bonded to the release film 13. The backing sheet 121 is bonded to the base 111 of the microneedle portion 11 through the adhesive film 121*a* without being separated, and bonded to the skin of the user through the adhesive film 121*a*. The release film 13 is suitable for covering a part of the adhesive film 121*a* to keep the adhesive film 121*a* clean so as to keep the adhesive film 121*a* sticky. Before use, the release film 13 should be removed.

Specifically, the backing sheet 121 is, for example, a film of polyurethane (PU), and the release film 13 is, for example, a release film of polyethylene terephthalate (PET), but the materials are not limited thereto. The adhesive film 121*a* may, for example, be selected from a material suitable for fitting with the human body.

When the dissolvable microneedle patch 1 is actually used, for example, the release film 13 connected to the backing sheet 121 is removed first to expose a part of the adhesive film 121*a*, and then the skin of the user is covered with the entire microneedle 112 patch, such that the microneedles 112 of the microneedle portion 11 pierce into the skin and the dissolvable microneedle patch 1 is bonded to the skin through the adhesive film 121*a* of the backing sheet 121.

Table 1 shows test results of different ratios of ingredients (sodium alginate and dextrin) in the microneedle portion 11.

TABLE 1

| No. | Ingredient 1 (wt %) | Ingredient 2 (wt %) | Ingredient 2/1 weight ratio | Film surface flatness | Releasability | Evaluation result |
|---|---|---|---|---|---|---|
| No. 1 | Sodium alginate 1% | Dextrin 0% | 0 | Curled | Not broken | NG |
| No. 2 | Sodium alginate 1.5% | Dextrin 0% | 0 | Curled | Not broken | NG |
| No. 3 | Sodium alginate 2.0% | Dextrin 0% | 0 | Curled | Not broken | NG |
| No. 4 | Sodium alginate 1.5% | Dextrin 0% | 0 | Slightly curled | Not broken | NG |
| No. 5 | Sodium alginate 1.5% | Dextrin 0.2% | 0.13 | Flat | Not broken | OK |
| No. 6 | Sodium alginate 1.5% | Dextrin 0.3% | 0.2 | Flat | Not broken | OK |
| No. 7 | Sodium alginate 1.5% | Dextrin 0.4% | 0.27 | Flat | Not broken | OK |
| No. 8 | Sodium alginate 1.5% | Dextrin 0.5% | 0.33 | Flat | Not broken | OK |
| No. 9 | Sodium alginate 1.5% | Dextrin 0.75% | 0.5 | Flat | Not broken | OK |
| No. 10 | Sodium alginate 1.5% | Dextrin 0.9% | 0.6 | Flat | Not broken | OK |
| No. 11 | Sodium alginate 1.5% | Dextrin 1% | 0.67 | Flat | Not broken | OK |
| No. 12 | Sodium alginate 1.5% | Dextrin 1.5% | 1 | Flat | Not broken | OK |
| No. 13 | Sodium alginate 1.5% | Dextrin 1.75% | 1.16 | Flat | Broken | NG |
| No. 14 | Sodium alginate 1.5% | Dextrin 2% | 1.33 | Flat | Broken | NG |

Table 1 shows results of tests to find out the proper ratio of the excipient ingredients in the mixture of the microneedle portion 11. No. 1 to No. 4 in Table 1 are examples where sodium alginate is added as the excipient to the aqueous solution for producing the microneedle portion 11. As can be seen, when the sodium alginate alone was used as the excipient, regardless of the percentage of the sodium alginate, the produced finished products (microneedle substrate 41, detailed in the subsequent method to produce the dissolvable microneedle patch) were not broken when being released from the mold, but their surfaces were curled. As a result, these finished products are not suitable for production (referring to film surface flatness in Table 1).

No. 5 in Table 1 is an example where the aqueous solution for producing the microneedle portion 11 uses a mixture containing only 1.5 wt % of sodium alginate with 0.2 wt % of dextrin as the excipient. As can be seen from the table, the produced finished product was not broken when being released from the mold (referring to releasability in Table 1), and the degree of curling was improved, but the finished product was still slightly curled (referring to film surface flatness in Table 1). As a result, this finished product is not suitable for use as the microneedle portion 11 of the dissolvable microneedle patch.

No. 6 to No. 12 in Table 1 are examples where the aqueous solution for producing the microneedle portion 11 uses a mixture containing only 1.5 wt % of sodium alginate respectively with 0.3 wt %, 0.4 wt %, 0.5 wt %, 0.75 wt %, 0.9 wt %, 1 wt % and 1.5 wt % of dextrin as the excipient. As can be seen, the produced finished products were not broken when being released from the mold (referring to releasability in Table 1) and had flat film surface (referring to film surface flatness in Table 1). As a result, these finished products are suitable for use as the microneedle portion 11 of the dissolvable microneedle patch.

No. 13 to No. 14 in Table 1 are examples where the aqueous solution for producing the microneedle portion 11 uses a mixture containing only 1.5 wt % of sodium alginate respectively with 1.75 wt % and 2 wt % of dextrin as the excipient. As can be seen, the produced finished products had flat film surface (referring to film surface flatness in Table 1), but were easily broken when being released from the mold (referring to releasability in Table 1). As a result, these finished products are not suitable for use as the microneedle portion 11 of the dissolvable microneedle patch.

Figure 2A:
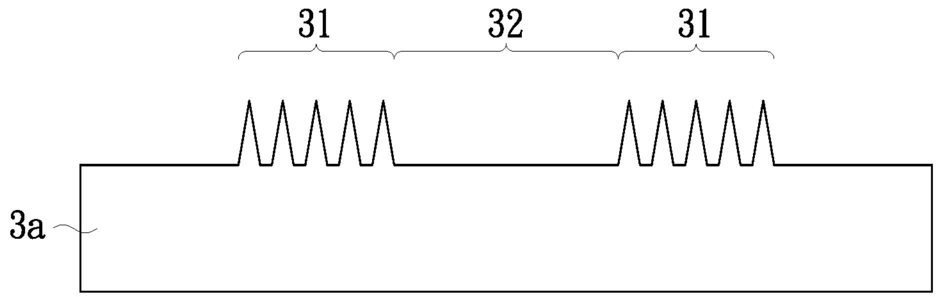
FIG. 2A to FIG. 2K are schematic views showing the flow of a method to produce the dissolvable microneedle patch according to an embodiment of the present invention.

FIG. 2A to FIG. 2K are schematic views showing the flow of a method to produce the dissolvable microneedle patch 1 according to an embodiment of the present invention. As shown in FIG. 2A, in an embodiment, the method to produce the aforementioned dissolvable microneedle patch 1 includes the following steps: A mold 3 is provided. The mold 3 is formed with a plurality of grooves 31 (referring to FIG. 2C). An aqueous solution 4 is injected into the mold 3 (referring to FIG. 2D). The aqueous solution 4 is, for example, an aqueous solution including the mixture used in the aforementioned dissolvable microneedle patch 1. The aqueous solution 4 is dried to form a microneedle substrate 41. The microneedle substrate 41 includes a plurality of microneedle portions 11. Each microneedle portion 11 includes a base 111 and a plurality of microneedles 112 (referring to FIG. 1). The microneedles 112 each have a shape corresponding to that of the grooves 31 each (referring to FIG. 2D to FIG. 2F). A plurality of patch materials are glued to the microneedle portion 11 (referring to FIG. 2G to FIG. 2H). The microneedle substrate 41 is cut to form a plurality of the dissolvable microneedle patches 1 (referring to FIG. 2J to FIG. 2K).

Specifically, referring to FIG. 2A, first, a first mold 3*a* is produced. A material of the first mold 3*a* may be a metal. The first mold has microneedles (not marked) having the shape and size corresponding to those of the microneedles 112 to be formed. According to the distribution positions of the microneedles, a plurality of microneedle areas 31 and blank areas 32 located between the microneedle areas 31 are formed on the first mold 3*a*. The range of the microneedle areas 31 may be set according to the range of the microneedle portion 11 on the dissolvable microneedle patch 1.

Figure 2B:
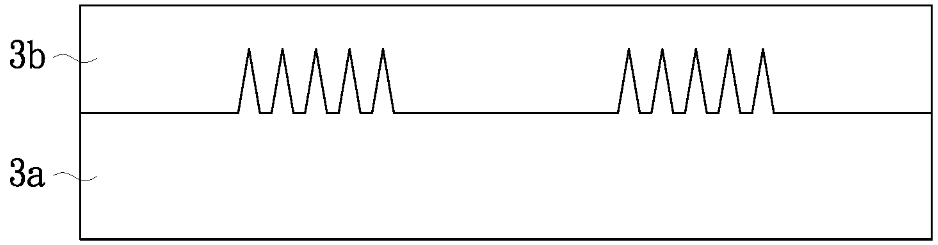
Figure 2C:
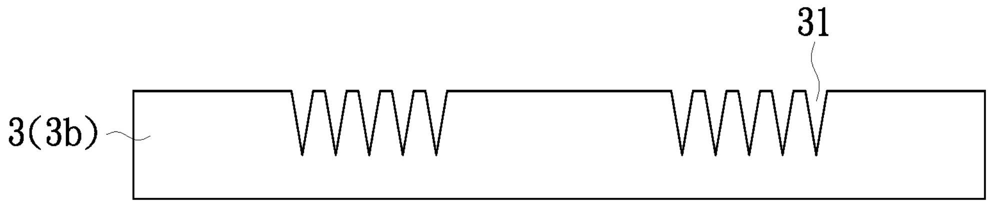

As shown in FIG. 2B, a second mold 3*b* having a shape corresponding to that of the first mold 3*a* is produced based on the first mold 3*a*, and the first mold 3*a* is separated from the second mold 3*b* (as shown in FIG. 2C). Grooves 31 corresponding to the microneedles on the first mold 3*a* are formed on the second mold 3*b*. In this embodiment, the periphery of the second mold 3*b* is, for example, formed with a frame (not shown) protruding from its surface, and accordingly, the center of the second mold 3*b* may be used for storing the aqueous solution 4 by the aid of the frame. A material of the second mold 3*b* is, for example, not limited thereto, polydimethylsiloxane (PDMS). The second mold 3*b* is used as the mold 3 for producing the microneedle portion 11 of the dissolvable microneedle patch 1.

Figure 2D:
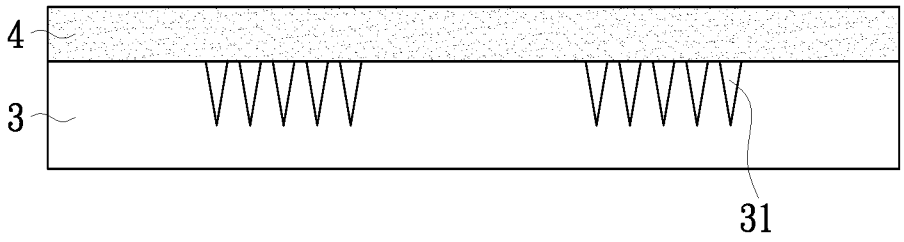

As shown in FIG. 2D, during the production of the microneedle portion 11, first, the aqueous solution 4 is injected into the mold 3. The aqueous solution 4, as described above, includes an excipient and a functional ingredient. The excipient includes sodium alginate and dextrin, and a weight ratio of the dextrin to the sodium alginate is 0.2 to 1. The aqueous solution 4 (which may be regarded as an aqueous solution of sodium alginate) has a viscosity of, for example, 15 to 5000 cps, which may be determined by adjusting the molecular weight of the sodium alginate.

Figure 2E:
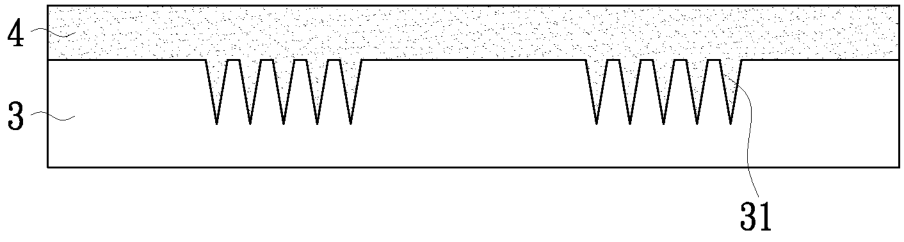

As shown in FIG. 2E, after the aqueous solution 4 is injected, debubbling is performed, which prevents bubbles from remaining in the grooves 31 due to the viscosity of the aqueous solution 4, causing incomplete shape of the microneedles 112 produced subsequently. The debubbling is, for example, vacuum debubbling at room temperature, but not limited thereto.

Figure 2F:
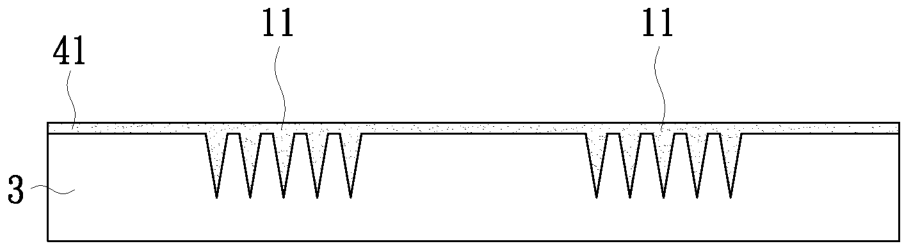

Next, as shown in FIG. 2F, the aqueous solution 4 is dried such that the aqueous solution 4 becomes solid to form the microneedle substrate 41. The aqueous solution 4 is dried, for example, at 30 to 60° C. for 1 to 6 hours, which may depend on the actual demands.

Figure 2G:
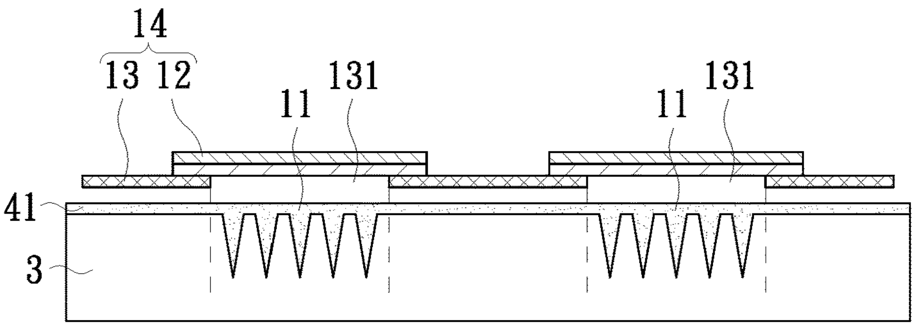

As shown in FIG. 2G, while the microneedle substrate 41 still remains on the mold 3, the microneedle substrate 41 is covered with a patch material. The patch material is, for example, a combined film 14 having a plurality of backing sheets 121 (for convenience of illustration, the backing sheets 121 are drawn as the patch portions 12 in FIG. 2G to FIG. 2K) and a release film 13. The release film 13 has a plurality of holes 131. Each backing sheet 121 covers one hole 131. The backing sheets 121 are bonded to the release film 13 through an adhesive film 121*a*, and each backing sheet 121 covers the surface of the release film 13 on the same side. Therefore, when the combined film 14 is bonded to the microneedle substrate 41, each backing sheet 121 and the microneedle substrate 41 are respectively located on two opposite sides of the release film 13. The size and position of each of the holes 131 in the release film 13 correspond to the size and position of the base 111 of the produced dissolvable microneedle patch 1.

Figure 2H:
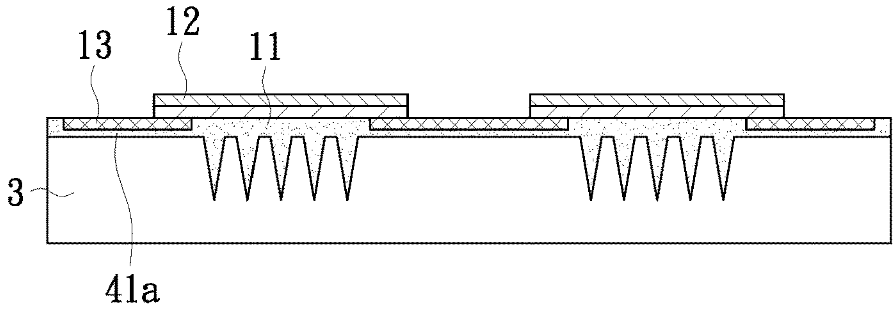
Figure 2I:
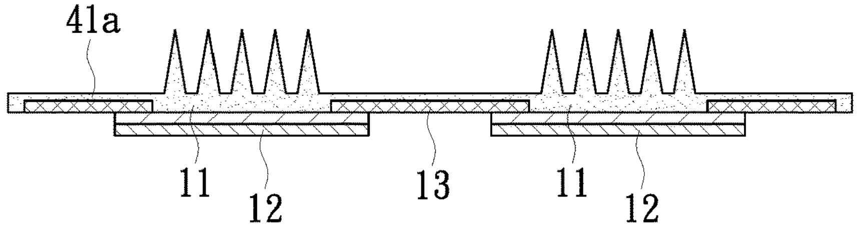

As shown in FIG. 2G and FIG. 2H, next, the combined film 14 is pressed such that the backing sheet 121 on the patch material is glued to the microneedle substrate 41. The part of the microneedle substrate 41 where the holes 131 are located forms the microneedle portion 11, and the part other than the microneedle portion 11 forms a remaining portion 41*a*. Then, as shown in FIG. 2I, a composition of the combined film 14 and the microneedle substrate 41 is released from the mold 3.

Figure 2J:
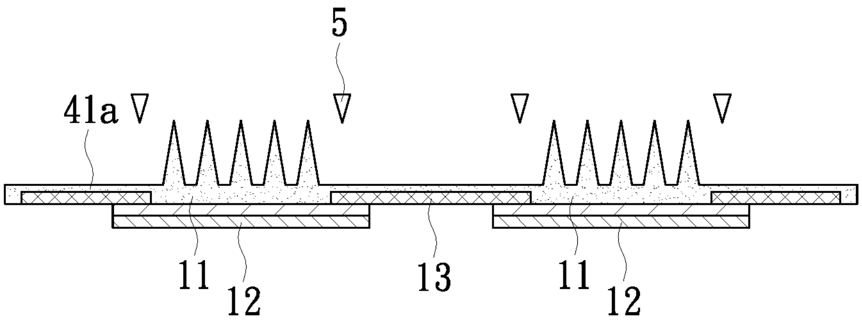
Figure 2K:
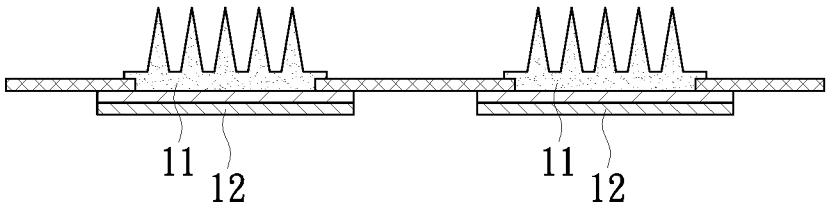

As shown in FIG. 2J and FIG. 2K, next, the remaining portion 41*a* is separated from the microneedle portion 11 by, for example, a cutter 5, and the remaining portion 41*a* is removed such that the dissolvable microneedle patch 1 is formed on the release film 13. The actual type of the cutter 5 may be selected according to demands, which is, for example, a solid cutter or a laser. As shown in FIG. 2K, through the above method, a plurality of the dissolvable microneedle patches 1 may be produced on one release film 13 at the same time, and these dissolvable microneedle patches 1 are connected with each other through the release film 13. In other embodiments, in the step of cutting the remaining portion 41*a*, the release film 13 may also be cut so as to produce a plurality of the dissolvable microneedle patches 1 that are separated from each other. The cutting manner may be determined according to the requirements on the product packaging, but is not limited thereto.

Based on the above, according to the dissolvable microneedle patch of the present invention, the weight ratio of the sodium alginate to the dextrin in the excipient is adjusted, so the base of the produced dissolvable microneedle portion has flat surface and low breaking tendency, and is suitable for a nice fit with the patch portion, and the produced dissolvable microneedle patch does not have the problem of curling film surface, skew or fractured microneedle structure, etc. According to the method to produce the dissolvable microneedle patch of the present invention, the weight ratio of the sodium alginate to the dextrin in the excipient is adjusted, so the produced microneedle patch has the advantages and features of the above-mentioned dissolvable microneedle patch.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A dissolvable microneedle patch, comprising:

a microneedle portion, having a base and a plurality of microneedles, the base having a first surface and a second surface opposite thereto, and the microneedles being connected to the first surface; and a patch portion, connected to the second surface;

wherein the microneedle portion is made from a mixture, the mixture comprises an excipient, the excipient comprises sodium alginate and dextrin, and a weight ratio of the dextrin to the sodium alginate is 0.2 to 1.

2. The dissolvable microneedle patch according to claim 1, wherein the microneedles have a height of 100 to 1500 μm.

3. The dissolvable microneedle patch according to claim 1, wherein the microneedles each have a shape of a pyramid or a cone.

4. The dissolvable microneedle patch according to claim 1, wherein the mixture further comprises a functional ingredient selected from hyaluronic acid, salicylic acid, vitamin C, nicotinic acid, vitamin B5, sulfur, *Centella asiatica*, vitamin E powder, ceramide, glycerol, GLP-1, insulin, acetaminophen and combinations thereof.

5. A method to produce a dissolvable microneedle patch, comprising:

providing a mold formed with a plurality of grooves;

injecting an aqueous solution into the mold;

drying the aqueous solution to form a microneedle substrate, the microneedle substrate comprising a plurality of microneedle portions, each of the microneedle portions comprising a base and a plurality of microneedles, and the microneedles each having a shape corresponding to each of the grooves;

gluing a plurality of patch materials to the microneedle portion; and cutting the microneedle substrate to form a plurality of the dissolvable microneedle patches;

wherein a mixture of an excipient and a functional ingredient is dissolved in the aqueous solution, the excipient comprises sodium alginate and dextrin, and a weight ratio of the dextrin to the sodium alginate is 0.2 to 1.

6. The method to produce the dissolvable microneedle patch according to claim 5, wherein the aqueous solution comprises 1.5% by weight of the sodium alginate.

7. The method to produce the dissolvable microneedle patch according to claim 5, wherein the aqueous solution of sodium alginate has a viscosity of 15 to 5000 cps.

8. The method to produce the dissolvable microneedle patch according to claim 5, wherein the aqueous solution is dried at 30 to 60° C. for 1 to 6 hours.

* * * * *